(12) United States Patent
Akahori et al.

(10) Patent No.: US 10,605,594 B2
(45) Date of Patent: Mar. 31, 2020

(54) METHOD AND APPARATUS FOR MEASURING THICKNESS OF ELECTROLYTE MEMBRANE

(71) Applicant: HONDA MOTOR CO., LTD., Minato-ku, Tokyo (JP)

(72) Inventors: Shigeto Akahori, Tochigi-ken (JP); Shohei Yoshida, Tochigi-ken (JP); Satoshi Hasegawa, Tochigi-ken (JP); Tomoko Tamai, Tochigi-ken (JP); Mai Yokoi, Tochigi-ken (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 16/142,041

(22) Filed: Sep. 26, 2018

(65) Prior Publication Data
US 2019/0101386 A1   Apr. 4, 2019

(30) Foreign Application Priority Data

Sep. 29, 2017   (JP) .................................. 2017-190241

(51) Int. Cl.
| | | |
|---|---|---|
| *G01N 23/223* | (2006.01) | |
| *G01B 15/02* | (2006.01) | |
| *H01M 8/1067* | (2016.01) | |
| *H01M 8/1004* | (2016.01) | |
| *H01M 8/00* | (2016.01) | |
| *H01M 8/1018* | (2016.01) | |

(52) U.S. Cl.
CPC ........... *G01B 15/02* (2013.01); *G01N 23/223* (2013.01); *H01M 8/004* (2013.01); *H01M 8/1004* (2013.01); *H01M 8/1067* (2013.01); *H01M 2008/1095* (2013.01)

(58) Field of Classification Search
None
See application file for complete search history.

(56) References Cited

U.S. PATENT DOCUMENTS

| | | | |
|---|---|---|---|
| 2008/0165924 A1* | 7/2008 | Wang | G01N 23/04 378/27 |
| 2011/0206973 A1 | 8/2011 | Brant et al. | |
| 2014/0021346 A1* | 1/2014 | Stoks | G01N 23/225 250/307 |
| 2015/0270567 A1 | 9/2015 | Tanuma et al. | |
| 2015/0362441 A1* | 12/2015 | Kulikovsky | G01N 23/083 378/51 |
| 2018/0328871 A1* | 11/2018 | Lee | G01B 11/06 |

FOREIGN PATENT DOCUMENTS

| | | |
|---|---|---|
| JP | 2012-506792 | 3/2012 |
| JP | 2015-195187 | 11/2015 |

* cited by examiner

*Primary Examiner* — Hoon K Song
(74) *Attorney, Agent, or Firm* — Amin, Turocy & Watson, LLP

(57) ABSTRACT

An electrolyte membrane thickness measurement apparatus includes a detecting medium supplying portion configured to emit a detecting medium, a detecting portion configured to detect a metal catalyst, and an analyzing unit. A thickness direction profile of a detection signal is generated by the detecting portion, and first and second inflection points are determined in the thickness direction profile based on the intensity of the detection signal by the analyzing unit. The distance between the first and second inflection points is evaluated as the thickness of the electrolyte membrane by the analyzing unit.

7 Claims, 4 Drawing Sheets

METHOD AND APPARATUS FOR MEASURING THICKNESS OF ELECTROLYTE MEMBRANE

CROSS-REFERENCE TO RELATED APPLICATION

This application is based upon and claims the benefit of priority from Japanese Patent Application No. 2017-190241 filed on Sep. 29, 2017, the contents of which are incorporated herein by reference.

BACKGROUND OF THE INVENTION

Field of the Invention

The present invention relates to a method and an apparatus for measuring a thickness of an electrolyte membrane in a membrane electrode assembly.

Description of the Related Art

A unit cell of a fuel cell is prepared by interposing a membrane electrode assembly between a pair of separators. The membrane electrode assembly contains an anode, a cathode, and a solid polymer electrolyte membrane interposed between the anode and the cathode. Each of the anode and the cathode has an electrode catalyst layer containing a metal catalyst, and further has a gas diffusion layer adjacent to the electrode catalyst layer. The electrode catalyst layer is arranged adjacent to the electrolyte membrane.

In general, manufacturers of such membrane electrode assemblies disclose a nominal thickness of the electrolyte membrane. However, for example, in a case where an impurity enters in between the gas diffusion layer and the electrode catalyst layer in the cathode, the electrode catalyst layer in the cathode is deformed or strained around the impurity, and the deformed portion is made closer to the electrode catalyst layer in the anode. As a result, the thickness of the electrolyte membrane becomes smaller than the nominal thickness locally at the position corresponding to the deformed portion. The fuel cell using the membrane electrode assembly having such a deteriorated electrolyte membrane may cause short circuit. Accordingly, in order to remove the membrane electrode assembly having the deteriorated electrolyte membrane, the thickness of the electrolyte membrane in the membrane electrode assembly is measured before the membrane electrode assembly is interposed between the separators.

A contact measurement apparatus such as Litematic (available from Mitutoyo Corporation) described in Japanese Laid-Open Patent Publication No. 2012-506792 (PCT) (see especially paragraph [0135]) has been known as an apparatus for measuring the thickness of the membrane electrode assembly. When the contact measurement apparatus is used, contact terminals are brought into contact with front and back surfaces of a subject, and the thickness of the subject is obtained from the distance between the contact terminals. However, although the total thickness of the anode, the electrolyte membrane, and the cathode can be measured by the contact measurement apparatus, the thickness of only the electrolyte membrane cannot be measured.

Also a scanning electron microscope may be used for measuring the thickness of the electrolyte membrane as described in Japanese Laid-Open Patent Publication No. 2015-195187 (see especially paragraph [0060]). With this microscope, the thickness of the electrolyte membrane in the membrane electrode assembly can be calculated based on a magnification and an apparent thickness of the electrolyte membrane in the observed field.

SUMMARY OF THE INVENTION

In the membrane thickness measurement using the scanning electron microscope, it is necessary to cut out a sample from the membrane electrode assembly. Thus, the measurement is a so-called destructive test. Since a part of the membrane electrode assembly is removed as the sample to carry out the measurement, the resultant membrane electrode assembly cannot be used for producing the unit cell. In other words, the scanning electron microscope cannot measure the thickness of the electrolyte membrane that is to be actually used (i.e., the electrolyte membrane after the thickness measurement cannot be put into practical use).

A principal object of the present invention is to provide a method capable of measuring a thickness of an electrolyte membrane in a membrane electrode assembly through a non-destructive test.

Another object of the present invention is to provide a method of measuring a thickness of an electrolyte membrane, which allows the membrane electrode assembly to be used practically, after the measurement of the electrolyte membrane thickness.

A further object of the present invention is to provide an electrolyte membrane thickness measurement apparatus usable for the above measurement method.

According to an aspect of the present invention, there is provided a method for measuring a thickness of an electrolyte membrane in a membrane electrode assembly containing a first electrode, a second electrode, and the electrolyte membrane sandwiched therebetween, the electrolyte membrane containing a solid polymer, the first electrode including a first electrode catalyst layer containing a metal catalyst, the second electrode including a second electrode catalyst layer containing a metal catalyst, the method comprising the steps of: supplying a detecting medium for detecting the metal catalyst in the first electrode catalyst layer and the second electrode catalyst layer to the membrane electrode assembly in a thickness direction from the first electrode catalyst layer to the second electrode catalyst layer to obtain a thickness direction profile of a detection signal; and determining a first inflection point and a second inflection point by an analyzing unit based on an intensity of the detection signal in the thickness direction profile, and evaluating a distance between the first inflection point and the second inflection point as the thickness of the electrolyte membrane.

According to another aspect of the present invention, there is provided an electrolyte membrane thickness measurement apparatus for measuring a thickness of an electrolyte membrane in a membrane electrode assembly containing a first electrode, a second electrode, and the electrolyte membrane sandwiched therebetween, the electrolyte membrane containing a solid polymer, the first electrode including a first electrode catalyst layer containing a metal catalyst, the second electrode including a second electrode catalyst layer containing a metal catalyst, the electrolyte membrane thickness measurement apparatus comprising: a detecting medium supplying portion configured to supply a detecting medium to detect the metal catalyst in the first electrode catalyst layer and the second electrode catalyst layer, to the membrane electrode assembly in a thickness direction from the first electrode catalyst layer to the second electrode catalyst layer; a detecting portion configured to detect the metal catalyst to obtain a thickness direction profile of a detection signal; and an analyzing unit configured to determine a first inflection point and a second inflection point based on an intensity of the detection signal in the thickness direction profile obtained by the detecting portion, and evaluate a distance between the first inflection point and the second inflection point as the thickness of the electrolyte membrane.

In the present invention, the metal catalyst in the membrane electrode assembly is detected by the detecting medium first, and the thickness of the electrolyte membrane is obtained based on the thickness direction profile of the detection signal at that time. Thus, in the present invention, the thickness of the electrolyte membrane in the membrane electrode assembly can be measured in a non-destructive test. Therefore, the membrane electrode assembly can be practically used for producing a fuel cell even after the thickness measurement for judging whether or not an impurity enters into the membrane electrode assembly. Consequently, short circuit of the fuel cell can be prevented.

It is preferred that the electrolyte membrane thickness measurement apparatus may further comprise a scanning unit configured to relatively scan the membrane electrode assembly by the detecting medium supplying portion and the detecting portion in a planar direction of the membrane electrode assembly. In this case, the detecting medium supplying portion and the detecting portion are relatively displaced in the planar direction of the membrane electrode assembly, whereby the thickness of the electrolyte membrane can be easily measured at a plurality of positions in the membrane electrode assembly successively.

It is preferred that a focal spot diameter of the detecting medium supplied from the detecting medium supplying portion may be smaller than a nominal thickness of the electrolyte membrane. In this case, the first inflection point and the second inflection point are clearly shown in the thickness direction profile of the detection signal, so that the thickness of the electrolyte membrane can be measured highly accurately.

For example, the detecting medium supplying portion may preferably be an X-ray emitting portion using an X-ray as the detecting medium. In this case, when the metal catalyst is irradiated with the X-ray, the metal catalyst produces a fluorescence. The detecting portion receives the fluorescence to generate the detection signal, whereby the above evaluation is carried out.

In the present invention, the metal catalyst in the membrane electrode assembly is detected by the detecting medium, and the thickness of the electrolyte membrane is obtained from the first inflection point and the second inflection point in the thickness direction profile determined based on the intensity of the detection signal in the thickness direction profile at that time. Thus, in the present invention, the thickness of the electrolyte membrane in the membrane electrode assembly can be measured in the non-destructive test.

Therefore, the membrane electrode assembly can be practically used for producing the fuel cell even after the thickness measurement for judging whether or not an impurity enters into the membrane electrode assembly. Consequently, short circuit of the fuel cell can be prevented.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

A preferred embodiment of a method for measuring a thickness of an electrolyte membrane according to the present invention and a related electrolyte membrane thickness measurement apparatus for the method will be described in detail below with reference to the accompanying drawings. Hereinafter, the electrolyte membrane thickness measurement apparatus may be referred to simply as a "thickness measurement apparatus", and a membrane electrode assembly may be referred to as an "MEA".

Figure 1:
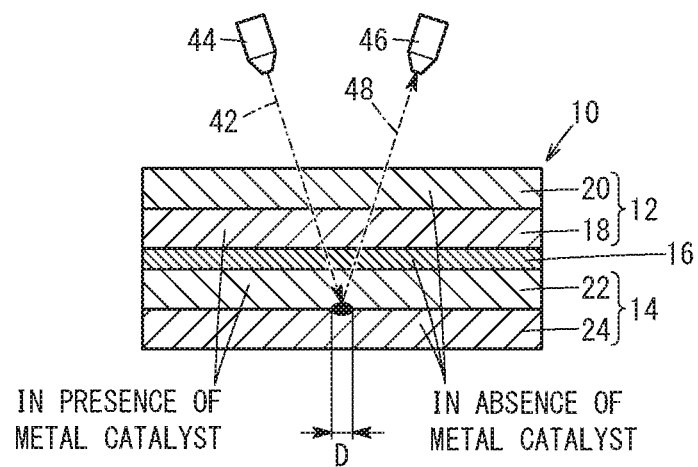
FIG. 1 is a schematic cross-sectional view of a membrane electrode assembly.

An MEA 10 will be described below with reference to FIG. 1. The MEA 10 has an anode 12 (a first electrode), a cathode 14 (a second electrode), and an electrolyte membrane 16 interposed between the anode 12 and the cathode 14. Although the anode 12 is used as an upper electrode and the cathode 14 is used as a lower electrode in FIG. 1, the electrodes may be reversed with each other.

The anode 12 contains a first electrode catalyst layer 18 adjacent to the electrolyte membrane 16, and further contains a first gas diffusion layer 20 located outside the first electrode catalyst layer 18. The first electrode catalyst layer 18 contains a metal catalyst for promoting an anode reaction for ionizing hydrogen atoms to generate protons. The metal catalyst is fixed or bonded by an ion-conducting polymer binder in the first electrode catalyst layer 18. Typical examples of the metal catalysts include platinum group metals such as Pt (platinum), Pd (palladium), and alloys thereof.

The metal catalyst may be supported on a carbon black or the like, and the catalyst-supporting carbon black or the like may be fixed or bonded by the ion-conducting polymer binder to form the first electrode catalyst layer 18. The anode reaction is represented by the following formula (1):

$$H_2 \rightarrow 2H^+ + 2e \qquad (1)$$

wherein e is an electron.

The first gas diffusion layer 20 contains a carbon material such as a carbon paper or a carbon cloth. When a fuel cell having the MEA 10 is operated, a fuel gas (such as a hydrogen gas) is supplied to the first gas diffusion layer 20. The hydrogen atoms in the fuel gas are transferred to the first electrode catalyst layer 18, and are used in the above anode reaction.

The cathode 14 has a structure similar to that of the anode 12. The cathode 14 contains a second electrode catalyst layer 22 adjacent to the electrolyte membrane 16, and further contains a second gas diffusion layer 24 located outside of the second electrode catalyst layer 22. The second electrode catalyst layer 22 contains a metal catalyst for promoting a cathode reaction for bonding oxygen atoms, protons, and electrons to generate water molecules. The metal catalyst is fixed or bonded by the ion-conducting polymer binder in the second electrode catalyst layer 22. The metal catalyst in the second electrode catalyst layer 22 may be similar to the metal catalyst in the first electrode catalyst layer 18, and typical examples of the metal catalysts in the second electrode catalyst layer 22 include platinum group metals such as Pt, Pd, and alloys thereof. The metal catalyst may be supported on a carbon black or the like, and the catalyst-supporting carbon black or the like may be fixed or bonded by the ion-conducting polymer binder to form the second electrode catalyst layer 22.

The second gas diffusion layer 24 contains a carbon material such as a carbon paper or a carbon cloth similarly to the first gas diffusion layer 20. When the fuel cell is operated, an oxygen-containing gas (such as a compressed air) is supplied to the second gas diffusion layer 24. The oxygen-containing gas is transferred to the second electrode catalyst layer 22, and is used in the above cathode reaction. The cathode reaction is represented by the following formula (2):

$$4H^+ + 4e + O_2 \rightarrow 2H_2O \qquad (2).$$

The electrolyte membrane 16 contains a proton-conductive solid polymer. Preferred examples of such solid polymers include perfluorosulfonic acid polymers. The protons generated in the first electrode catalyst layer 18 are moved through the electrolyte membrane 16 to the second electrode catalyst layer 22.

A thickness measurement apparatus according to the embodiment will be described below with reference to FIG. 2.

Figure 2:
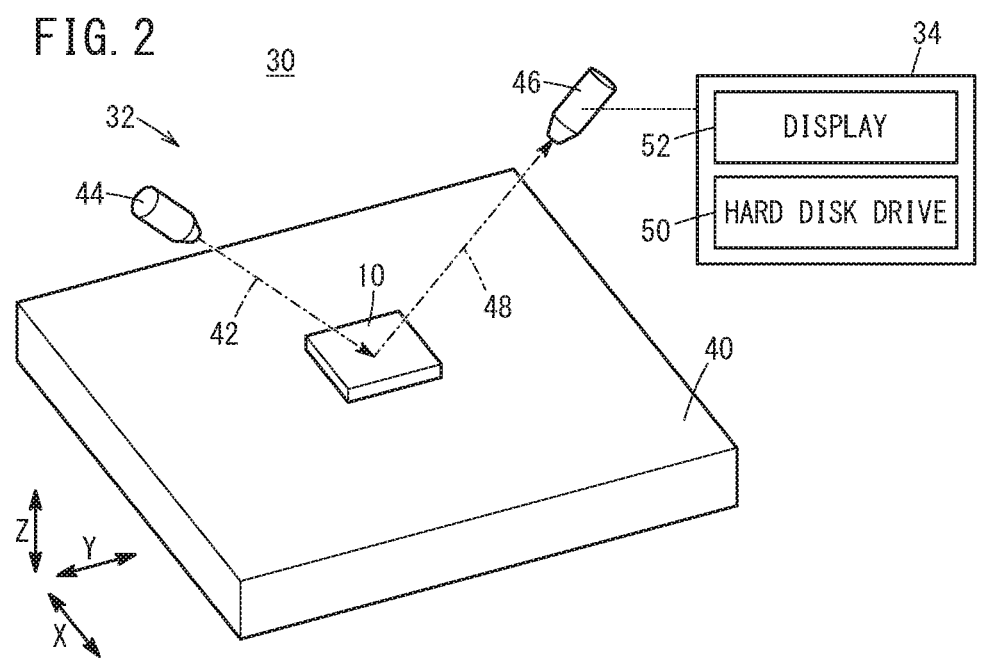
FIG. 2 is a view illustrating a schematic system configuration of an electrolyte membrane thickness measurement apparatus according to an embodiment of the present invention.

FIG. 2 is a view illustrating a schematic system configuration of a thickness measurement apparatus 30 according to the present embodiment. The thickness measurement apparatus 30 has a confocal fluorescent X-ray analysis mechanism 32 and an analyzing personal computer (PC) 34.

The confocal fluorescent X-ray analysis mechanism 32 has a table 40 on which the MEA 10 is placed, an X-ray emitting portion 44 (a detecting medium supplying portion) for emitting (supplying) an X-ray 42 as a detecting medium, and a detecting portion 46 for detecting the metal catalyst. The table 40 is an uppermost bed of an XYZ stage, and can be displaced by an actuator (not shown) in an X direction (a horizontal direction), a Y direction (a horizontal direction), and a Z direction (a vertical direction) shown in FIG. 2. When the table 40 is displaced, the MEA 10 placed on the table 40 is integrally displaced. Thus, the table 40 is a scanning unit for scanning the MEA 10 in the planar direction (the X and Y directions) and the thickness direction (the Z direction).

The X-ray emitting portion 44 acts to emit the X-ray 42 toward the MEA 10. The X-ray 42 is applied to the MEA 10 at a predetermined angle to the planar direction of the MEA 10. When the metal catalyst is irradiated with the X-ray 42, the metal catalyst produces a fluorescence 48. The detecting portion 46 is inclined at a predetermined angle to the planar direction of the MEA 10. When the detecting portion 46 detects the fluorescence 48, the detecting portion 46 generates a detection signal indicating that the fluorescence 48 is detected.

The PC 34 has a hard disk drive 50, on which an analysis software is installed as an analyzing means (unit). Under control of the analysis software, the emission of the X-ray 42 is started and stopped, and the table 40 (the XYZ stage) is moved (scanned). When the hard disk drive 50 receives the detection signal, the intensity of the detection signal is differentiated, and the thickness of the electrolyte membrane 16 is evaluated based on the differential results.

The PC 34 further has a display 52. The analysis results based on the differential results of the detection signal are shown on the display 52.

The thickness measurement apparatus 30 of the present embodiment is constructed basically as described above. Next, operations and effects of the thickness measurement apparatus 30 will be described below together with the related thickness measurement method of the embodiment.

In the membrane thickness measurement, first, the MEA 10 is placed on the table 40. Next, the table 40 is appropriately scanned, the MEA 10 is moved closer to the X-ray emitting portion 44 and the detecting portion 46, and the scanning is stopped. Then, while the table 40 is displaced in the Z direction (the thickness direction of the MEA 10) (i.e., while the table 40 is raised), the X-ray 42 is emitted from the X-ray emitting portion 44 toward the MEA 10.

In this process, it is preferred that the focal spot diameter D of the X-ray 42 (see FIG. 1) is smaller than a nominal thickness T of the electrolyte membrane 16. In this case, first and second inflection points to be hereinafter described can be obtained easily.

The X-ray 42 is applied through the first gas diffusion layer 20 to the inside of the MEA 10. Thus, a focal spot of the X-ray 42 is formed inside the first gas diffusion layer 20. As described above, the first gas diffusion layer 20 contains the carbon material such as the carbon paper or the carbon cloth. Therefore, when the first gas diffusion layer 20 is irradiated with the X-ray 42, the carbon material does not emit the fluorescence 48.

As the table 40 is raised, the focal spot of the X-ray 42 is moved into the first electrode catalyst layer 18. The first electrode catalyst layer 18 contains the metal catalyst such as Pt or Pd. Therefore, when the first electrode catalyst layer 18 is irradiated with the X-ray 42, the metal catalyst emits the fluorescence 48. The fluorescence 48 is emitted toward the outside of the MEA 10 (see FIG. 1), and applied to the detecting portion 46. When the detecting portion 46 receives the fluorescence 48, the detecting portion 46 generates the detection signal indicating that the fluorescence 48 is applied, and the detection signal is sent to the hard disk drive 50. When the hard disk drive 50 receives the detection signal, the analysis software recognizes the presence of the metal catalyst.

As the table 40 is further raised, the focal spot of the X-ray 42 is moved into the electrolyte membrane 16. The electrolyte membrane 16 is a thin membrane containing the solid polymer. Therefore, when the electrolyte membrane 16 is irradiated with the X-ray 42, the electrolyte membrane 16 does not emit the fluorescence 48. Thus, the detecting portion 46 generates no detection signals in this step.

As the table 40 is still further raised, the focal spot of the X-ray 42 is moved into the second electrode catalyst layer 22. In FIG. 1, the focal spot of the X-ray 42 reaches an interface between the second electrode catalyst layer 22 and the second gas diffusion layer 24.

The second electrode catalyst layer 22 contains the metal catalyst such as Pt or Pd. Therefore, when the second electrode catalyst layer 22 is irradiated with the X-ray 42, the metal catalyst emits the fluorescence 48. When the detecting portion 46 receives the fluorescence 48, the detecting portion 46 generates the detection signal, and the detection signal is sent to the hard disk drive 50. As a result, the analysis software recognizes the presence of the metal catalyst.

As the table 40 is still further raised, the focal spot of the X-ray 42 is moved into the second gas diffusion layer 24. Since the second gas diffusion layer 24 contains the carbon material, the fluorescence 48 is not emitted.

Figure 3:
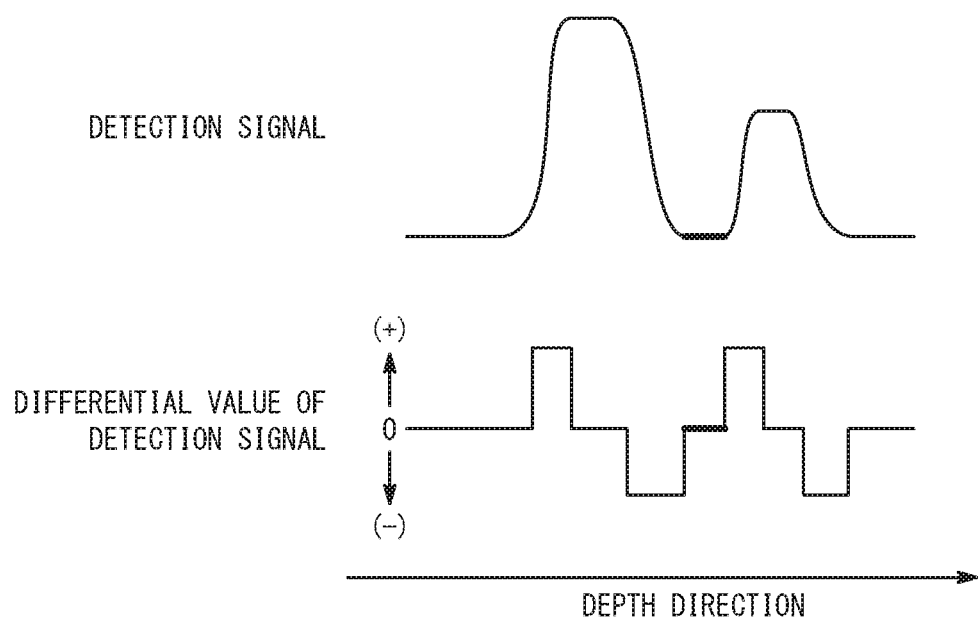
FIG. 3 is a diagram showing a thickness direction profile of a detection signal and a graph of a differential value obtained by differentiating the detection signal.

A predetermined portion of the MEA 10 is scanned in the thickness direction with the X-ray 42 in this manner. A thickness direction profile is made by the analysis software based on the intensity of the received detection signal. FIG. 3 is a diagram showing an example of the thickness direction profile of the detection signal. In FIG. 3, the intensity of the detection signal from the second electrode catalyst layer 22 is lower than that from the first electrode catalyst layer 18. This is because the incidence of the X-ray 42 and the emission of the fluorescence 48 are obstructed by the electrolyte membrane 16, the first electrode catalyst layer 18, and the first gas diffusion layer 20 disposed above the second electrode catalyst layer 22.

As described above, the detection signal is generated only when the focal spot of the X-ray 42 is located in the first electrode catalyst layer 18 or the second electrode catalyst layer 22. Therefore, the intensity of the detection signal is increased when the focal spot of the X-ray 42 is moved from the first gas diffusion layer 20 to the first electrode catalyst layer 18, and the intensity is reduced when the focal spot is moved from the first electrode catalyst layer 18 to the electrolyte membrane 16. Furthermore, the intensity is increased again when the focal spot is moved from the electrolyte membrane 16 to the second electrode catalyst layer 22, and the intensity is reduced again when the focal spot is moved from the second electrode catalyst layer 22 to the second gas diffusion layer 24. It is to be understood that the intensity is substantially constant while the focal spot is located in the first electrode catalyst layer 18 or the second electrode catalyst layer 22.

The varying intensity of the detection signal in the thickness direction profile is differentiated by the analysis software. Also a differential graph showing the change in the differential value is shown in FIG. 3.

In the differential graph, the differential value of 0 means that the intensity of the detection signal is constant. When the state is changed from a state in which no detection signal is received to a state in which a detection signal is received, the differential value is changed from 0 to a positive (+) value. While a detection signal with constant intensity is received, the differential value is changed from a positive value to 0. When this state is changed to a state in which no detection signal is received, the differential value is changed from 0 to a negative (−) value while the intensity is reduced.

Furthermore, while the state in which no detection signal is received is continued, the detection signal has the constant intensity of 0, whereby the differential value is changed from a negative value to 0. When this state is changed to a state in which a detection signal is received, the differential value is changed from 0 to a positive value while the intensity is increased.

As is clearly understood from the above description, the differential value is 0 when the focal spot of the X-ray 42 is located in the first electrode catalyst layer 18. The differential value is changed from 0 to a negative value when the focal spot is moved from the first electrode catalyst layer 18 to the electrolyte membrane 16. The differential value is changed from a negative value to 0 when the focal spot is located in the electrolyte membrane 16. The differential value is changed from 0 to a positive value when the focal spot is moved from the electrolyte membrane 16 to the second electrode catalyst layer 22. Therefore, the depth (thickness) at which the differential value is changed from the negative value to 0 and the depth (thickness) at which the differential value is then changed from 0 to the positive value can be measured. It should be noted that in a case where the focal spot diameter D is equal to or larger than the nominal thickness T of the electrolyte membrane 16, the change from 0 to the positive value cannot be clearly observed. Therefore, it is preferred that the focal spot diameter D is smaller than the nominal thickness T of the electrolyte membrane 16 to avoid the problem.

The differential value is changed at an inflection point at which the detection signal is changed from an increasing state to a decreasing state or from the decreasing state to the increasing state. By using the analysis software, the depth at which the differential value is changed from the negative value to 0 is obtained as a first inflection point, and the depth at which the differential value is then changed from 0 to the positive value is obtained as a second inflection point. The distance between the first inflection point and the second inflection point (the difference between the two depths) is measured as the thickness of the electrolyte membrane 16. In FIG. 3, a portion indicating the thickness of the electrolyte membrane 16 is shown by a bold line.

Thus obtained thickness is shown on the display 52, and also the differential graph is shown as required. An operator can read the information on the display 52 to know the thickness of the electrolyte membrane 16.

Thereafter, the table 40 is lowered in the Z direction, and is displaced in either one or both of the X and Y directions. Thus, a portion to be irradiated with the X-ray 42 is changed in the MEA 10. Then, the thickness in the irradiated portion can be measured in the same manner as above.

As described above, in this embodiment, after the MEA 10 is produced, the thickness of the electrolyte membrane 16 in the MEA 10 can be measured by a non-destructive test. Therefore, even after the thickness measurement, the MEA 10 can be interposed between a pair of separators to prepare a unit cell, and a fuel cell stack can be produced with a plurality of stacked unit cells.

Furthermore, since the table 40 is the uppermost bed of the XYZ stage in this embodiment, the thickness of the electrolyte membrane 16 can be measured at a plurality of positions in the MEA 10 successively.

Figure 4:
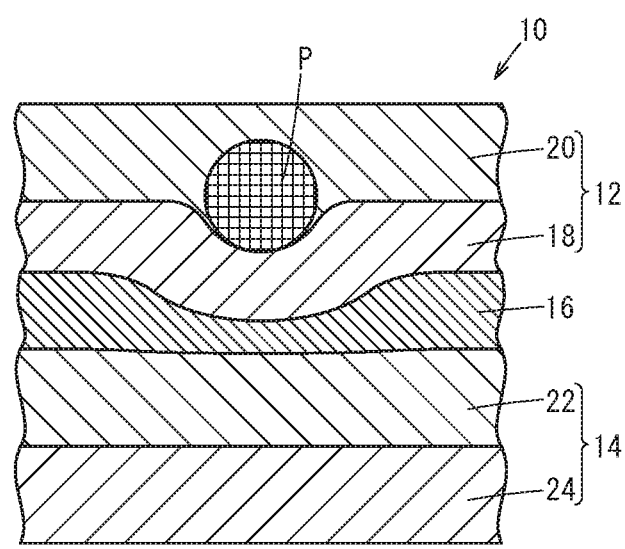
FIG. 4 is an enlarged cross-sectional view of a principal part of the membrane electrode assembly and an impurity entering thereinto.

As shown in FIG. 4, an impurity P sometimes enters in between the first gas diffusion layer 20 and the first electrode catalyst layer 18. In this case, the first electrode catalyst layer 18 is deformed or strained in the vicinity of the impurity P, and the deformed portion is made closer to the second electrode catalyst layer 22. Therefore, the measured thickness is locally smaller than the nominal thickness T in the deformed portion. In this case, the MEA 10 is recognized as defective and removed. Thus, such an MEA 10 is not used for producing the unit cell. Consequently, short circuit can be prevented in the fuel cell stack effectively.

The present invention is not particularly limited to the above embodiment, and various changes and modifications may be made therein without departing from the scope of the invention.

For example, in the above embodiment, the X-ray emitting portion 44 and the detecting portion 46 are fixed, whereas the table 40 is movable. Conversely, the table 40 may be fixed, and the X-ray emitting portion 44 and the detecting portion 46 may be displaced in the X, Y, and Z directions.

In addition, the detecting medium emitting from the detecting medium supplying portion may be an ultrasonic wave, a laser, etc.

What is claimed is:

1. A method for measuring a thickness of an electrolyte membrane in a membrane electrode assembly containing a first electrode, a second electrode, and the electrolyte membrane sandwiched therebetween, the electrolyte membrane containing a solid polymer, the first electrode including a first electrode catalyst layer containing a metal catalyst, the second electrode including a second electrode catalyst layer containing a metal catalyst, the method comprising the steps of:

supplying a detecting medium for detecting the metal catalyst in the first electrode catalyst layer and the second electrode catalyst layer to the membrane electrode assembly in a thickness direction from the first electrode catalyst layer to the second electrode catalyst layer to obtain a thickness direction profile of a detection signal; and determining a first inflection point and a second inflection point by an analyzing unit based on an intensity of the detection signal in the thickness direction profile, and evaluating a distance between the first inflection point and the second inflection point as the thickness of the electrolyte membrane.

2. The method according to claim 1, further comprising relatively scanning the membrane electrode assembly by a detecting medium supplying portion configured to supply the detecting medium and a detecting portion configured to detect the metal catalyst, in a planar direction of the membrane electrode assembly.

3. An electrolyte membrane thickness measurement apparatus for measuring a thickness of an electrolyte membrane in a membrane electrode assembly containing a first electrode, a second electrode, and the electrolyte membrane sandwiched therebetween, the electrolyte membrane containing a solid polymer, the first electrode including a first electrode catalyst layer containing a metal catalyst, the second electrode including a second electrode catalyst layer containing a metal catalyst, the electrolyte membrane thickness measurement apparatus comprising:

a detecting medium supplying portion configured to supply a detecting medium to detect the metal catalyst in the first electrode catalyst layer and the second electrode catalyst layer, to the membrane electrode assembly in a thickness direction from the first electrode catalyst layer to the second electrode catalyst layer;

a detecting portion configured to detect the metal catalyst to obtain a thickness direction profile of a detection signal; and an analyzing unit configured to determine a first inflection point and a second inflection point based on an intensity of the detection signal in the thickness direction profile obtained by the detecting portion, and evaluate a distance between the first inflection point and the second inflection point as the thickness of the electrolyte membrane.

4. The electrolyte membrane thickness measurement apparatus according to claim 3, wherein a focal spot diameter of the detecting medium supplied from the detecting medium supplying portion is smaller than a nominal thickness of the electrolyte membrane.

5. The electrolyte membrane thickness measurement apparatus according to claim 3, wherein the detecting medium supplied from the detecting medium supplying portion is an X-ray.

6. The electrolyte membrane thickness measurement apparatus according to claim 5, wherein the detecting portion is configured to detect a fluorescence.

7. The electrolyte membrane thickness measurement apparatus according to claim 3, further comprising a scanning unit configured to relatively scan the membrane electrode assembly by the detecting medium supplying portion and the detecting portion, in a planar direction of the membrane electrode assembly.

* * * * *